(12) United States Patent
Urbanski

(10) Patent No.: US 6,183,496 B1
(45) Date of Patent: Feb. 6, 2001

(54) COLLAPSIBLE HEMOSTATIC PLUG

(75) Inventor: Jeffrey Urbanski, Sparta, NJ (US)

(73) Assignee: Datascope Investment Corp., Montvale, NJ (US)

( * ) Notice: Under 35 U.S.C. 154(b), the term of this patent shall be extended for 0 days.

(21) Appl. No.: 09/184,170

(22) Filed: Nov. 2, 1998

(51) Int. Cl.$^7$ ................................................. A61B 17/04
(52) U.S. Cl. ............................................ 606/213; 606/151
(58) Field of Search .................... 606/213, 215, 606/151, 153, 192, 198; 623/1, 11, 12

(56) References Cited

U.S. PATENT DOCUMENTS

| | | | |
|---|---|---|---|
| 5,254,133 | * 10/1993 | Seid | 606/215 |
| 5,310,407 | 5/1994 | Casale | 604/51 |
| 5,312,435 | 5/1994 | Nash et al. | 606/213 |
| 5,326,350 | 7/1994 | Li | 623/11 |
| 5,330,445 | 7/1994 | Haaga | 604/265 |
| 5,334,217 | * 8/1994 | Das | 606/213 |
| 5,437,631 | 8/1995 | Janzen | 604/49 |
| 5,456,693 | 10/1995 | Conston et al. | 606/912 |
| 5,522,840 | 6/1996 | Krajicek | 606/213 |
| 5,591,204 | 1/1997 | Janzen et al. | 606/213 |
| 5,645,565 | * 7/1997 | Rudd et al. | 606/213 |
| 5,653,755 | * 8/1997 | Ledergerber | 623/8 |
| 5,938,682 | * 8/1999 | Hojeibane et al. | 606/198 |

* cited by examiner

Primary Examiner—Michael Buiz
Assistant Examiner—Vikki Hoa B. Trinh
(74) Attorney, Agent, or Firm—Abraham Ronai (57) ABSTRACT

A hemostatic plug for sealing wounds in blood vessels comprising a tubular or spring-like body capable of buckling or collapsing upon application of a threshold axial force and having a fretted distal end. A collapsed portion of the plug lodges into the tissue tract and thus acts as a foothold allowing the plug to maintain continuous pressure on the puncture site necessary for a quick effective closure of the wound. Furthermore, collapse of the plug minimizes the chance of arterial penetration.

14 Claims, 8 Drawing Sheets

COLLAPSIBLE HEMOSTATIC PLUG

BACKGROUND OF THE INVENTION

1. Field of the Invention

The invention relates to a method and device for sealing a puncture wound in a blood vessel. More particularly, the invention relates to a collapsible biodegradable collagen plug for sealing a puncture wound in a blood vessel that minimizes the risk of blood vessel entry and that maintains pressure on the puncture site in the blood vessel.

2. Description of the Prior Art

In certain medical procedures, such as cardiac catheterization, dilation and counterpulsation, a catheter or other device is inserted into an artery, most commonly by percutaneous methods, and then fed through the arterial tree to the site where needed, frequently, the region of the heart. The site usually selected for insertion of the catheter is the groin, because the femoral artery in that region is relatively easy to locate.

These procedures are normally initiated by insertion of an angiographic needle, followed by passing a guide wire through that needle into the artery. The needle is then removed leaving the guide wire in place. Next, a sheath-dilator set is passed over the guide wire into the artery in order to enlarge the opening sufficiently to permit entry of the catheter or other device. The dilator is then removed, leaving the sheath or guide cannula in place. The catheter or other device can then be inserted through the cannula with full confidence that when it emerges from the distal end it will be within the lumen of the artery.

It should be understood that the subject invention is independent of the blood vessel involved. While it is expected that the femoral artery will be the most commonly used blood vessel, use of other arteries as well as veins is anticipated as well.

After a procedure, for example, counterpulsation, has been completed, the sheath must be removed and the wound closed. Often, this can be accomplished simply by the application of digital pressure, generally augmented by the use of a pressure dressing. Customarily, pressure must be applied for at least ½ hour, and frequently for much longer than that. While pressure dressings often suffice, it is not uncommon for additional devices, such as sandbags, to be needed. In addition, during this period the patient must be immobilized, lest movement interfere with the closing process. Because of the pressure required, the time during which it must be applied and the need for immobilization, the procedure is painful and uncomfortable. The procedure also requires prolonged personal attention of a health care professional. Finally, wound closures accomplished in this manner are prone to reopen unexpectedly long after closure appears to have been completed. Patients are therefore often required to remain in the hospital for 24 hours or longer.

A device for sealing the wound, overcoming many of the above mentioned problems, is disclosed in U.S. Pat. No. 5,591,204 and is known in the medical field under Datascope Corp.'s VasoSeal® trademark. The VasoSeal® product comprises a charge of hemostatic material and a hollow sheath adapted to pass through the tissue channel of a patient, the sheath having a cross sectional profile larger than the puncture in the patient's blood vessel. The Vasoseal® product places the hemostatic material in the hollow sheath and advances the hemostatic material through the sheath to the outside of the vessel wall around the puncture. The preferred embodiment of the hemostatic material is a compressed cylinder or plug of collagen in which the distal most portion is fluffed. The plug is designed to mushroom slightly when the plug contacts the exterior wall of the artery and the stiff proximal end lodges in the tissue tract thus holding the expanded distal end in place on the artery. Aside from providing greater puncture area coverage the fluffing of the distal end also serves the purpose of exposing more hemostatic fibers to the blood thus allowing the hemostatic material to react more readily with the blood.

U.S. Pat. Nos. 5,330,445 and 5,552,840 disclose a tubular sheath which is slidably disposed over a tubular medical device and which is positioned at a body access site. The sheath is deposited within a patient to assist in sealing the wound caused by the tubular medical device and inhibit internal and external bleeding. Despite the wound sealing assistance provided, these wound sealing sheaths suffer a number of drawbacks, including the possibility of allowing the sheath to enter the artery. The sheath may enter the artery if the distal tip of the sheath does not mushroom out far or is not large enough to engage the puncture site at the exterior wall of the artery. In this instance the proximal end of the plug transmits the insertion force provided by the insertion device to the distal end of the plug allowing the distal tip to penetrate the puncture site and thus enter the artery. Entrance of the plug into the artery is dangerous for a number of reasons. Entrance of the distal tip of the plug, or the entire plug, into the artery obstructs blood passage in the artery and emboli formation on the plug further obstructs blood flow. Furthermore, emboli may break off the distal tip of the plug and flow downstream. Free floating emboli must be removed surgically to prevent decreased circulation to distal extremities.

Another major disadvantage of the above mentioned wound sealing devices is that they rely primarily on the friction force between the patient's tissue tract wall and the plug and slight swelling of the plug itself to maintain the position of the plug and its pressure on the puncture site. As a result, the plug may be dislodged from the tissue tract with minimal force. Furthermore, the pressure on the artery, required for rapid puncture closure, is lost quickly after the insertion device is removed.

While the foregoing wound closure devices may be suitable for the particular purposes employed, or for general use, they would not be as suitable for the purposes of the present invention as disclosed hereafter.

SUMMARY OF THE INVENTION

Accordingly, it is an object of the invention to produce an improved hemostatic plug which quickly seals a puncture in an artery without being prone to entering the artery or being easily dislodged from the artery.

It is another object of the invention to produce an improved hemostatic plug which applies a continuous pressure to the arterial puncture site.

It is a further object of the invention to produce a economical and efficient method for fabricating an improved hemostatic plug.

The invention is a hemostatic plug for sealing wounds in blood vessels comprising a tubular or spring-like body capable of buckling or collapsing upon application of a threshold axial force and having a fretted distal end. A collapsed portion of the plug lodges into the tissue tract and thus acts as a foothold allowing the plug to maintain continuous pressure on the puncture site necessary for a quick effective closure of the wound. Furthermore, collapse of the plug minimizes the chance of arterial penetration.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1A:
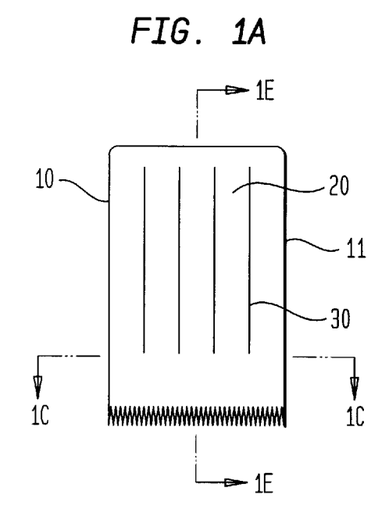
FIG. 1A is a plan view of an improved hemostatic plug.

FIG. 1A illustrates a plan view of an improved hemostatic plug 11 comprising a tube 10 having longitudinal radial expanding wings 20 extending from a point distal to the proximal end to a point proximal to the distal end of the plug 11. The wings 20 are formed by longitudinal lacerations 30 extending from a point distal to the proximal end to a point proximal to the distal end of the plug 11. The distal end of the plug 11 is fretted.

Figure 1B:
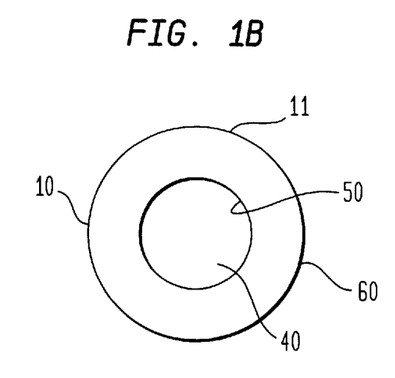
FIG. 1B is a top view of the proximal non-fretted end of the plug of FIG. 1A.

FIG. 1B illustrates a top view of the proximal non-fretted end of the plug 11. A lumen 40 extends from the proximal non-fretted end of the plug 11 to the distal fretted end of the plug 11. The tube has an inner surface 50 and an outer surface 60.

Figure 1C:
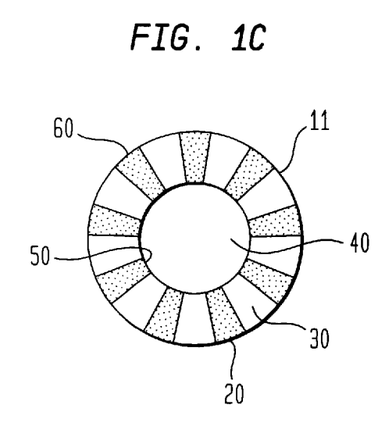
FIG. 1C is a transverse cross sectional view of the plug taken along lines 1C—1C.

FIG. 1C illustrates a transverse cross sectional view of the plug 11 taken along lines 1C–1C. The longitudinal lacerations 30 extend depthwise from the outer surface 60 to the inner surface 50 of the tube 10.

Figure 1D:
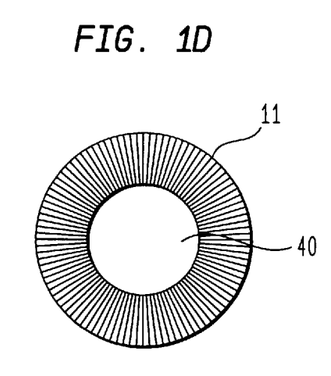
FIG. 1D is a bottom view of the fretted end of the plug.

FIG. 1D illustrates a bottom view of the fretted end of the plug 11.

Figure 1E:
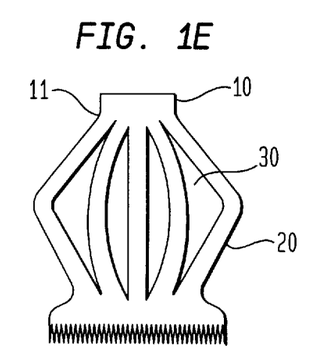
FIG. 1E is a longitudinal cross sectional view of the plug in a semi-collapsed form taken along lines 1E—1E in FIG. 1A.

FIG. 1E illustrates a longitudinal cross section of the plug 11 in a semi-collapsed form taken along lines 1E–1E in FIG. 1A. The distance between the proximal and distal ends of the plug 11 has decreased and as a result the wings 20 have buckled and radially expanded.

Figure 1F:
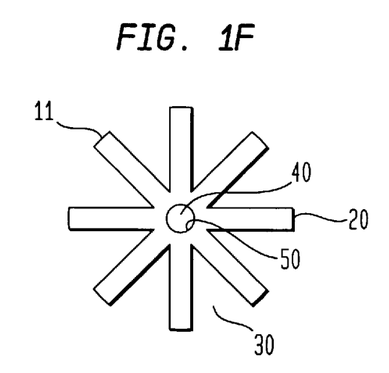
FIG. 1F is a top view of the proximal non-fretted end of the plug in its collapsed form.

FIG. 1F illustrates a top view of the proximal non-fretted end of the plug 11 in FIG. 1A in its collapsed form.

Figure 2:
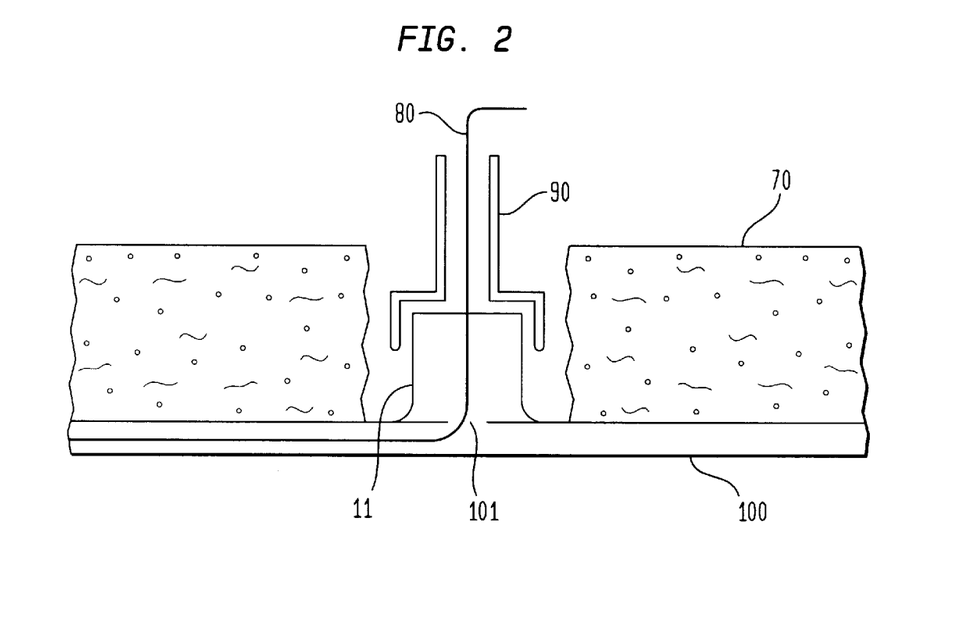
FIG. 2 is a cross sectional view of a patient's leg and the plug being inserted over a guide wire into said patient's leg.

FIG. 2 illustrates a cross sectional view of a patient's leg 70 and the plug 11, inserted over a guide wire 80, into said patient's leg 70. FIG. 2 illustrates the result of the first insertion step of the plug 11. The proximal end of the plug 11 is in contact with an insertion device 90 which provides axial insertion force to the plug 11. The distal fretted end of the plug 11 has totally covered a puncture 101 in a blood vessel 100 in the patient's leg 70 and has conformed to the surface of the blood vessel 100. The collapse of the fretted end and expansion of the plug 11 itself have occluded the lumen 40 (FIGS. 1B–1D). Aside from allowing the distal end of the plug 11 to conform to the surface of the blood vessel 100 and occluding the lumen 40, fretting the distal end of the plug 11 also serves the purpose of exposing more hemostatic fibers to the blood thus allowing the hemostatic material to react more readily with the blood.

Figure 3:
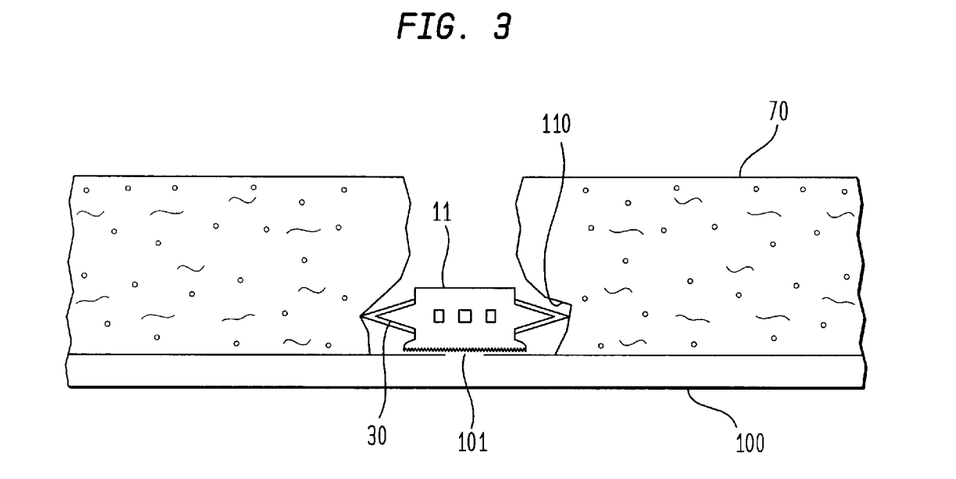
FIG. 3 illustrates a cross sectional view of a patient's leg and the plug in its inserted collapsed form.

FIG. 3 illustrates a cross sectional view of the patient's leg 70 and the plug 11 in its collapsed form. After the surgeon, via the insertion device 90 (as shown in FIG. 2), applies a threshold axial force to the plug 11, the wings 20 collapse and lodge between the artery and surrounding tissue 110. The now fixed plug 11 applies continuous pressure to the blood vessel 100. The plug 11 herein disclosed is more effective in sealing punctures than prior art plugs because of its ability to apply continuous pressure to the puncture 101 in the blood vessel 100. Prior art plugs rely only on the friction between the outer surface of the plug and the tissue tract to maintain the position of the plug relative to the blood vessel and thus maintain pressure on the blood vessel. Thus the lodging of the wings 20 into the surrounding tissue 110 is an important feature of the present invention.

The collapse of the plug 11, and the resultant lack of axial insertion resistance, indicates to the surgeon that the plug 11 is properly positioned and that he or she should terminate application of axial pressure. Any excessive insertion force, applied after the initial collapse of the plug 11, is transposed into radial expansion of the wings 20 not linear movement (the distal fretted end remains relatively fixed). Thus, the collapsibility feature of the plug 11 minimizes the potential for arterial insertion of the plug 11. Furthermore, the radial expansion of the wings 20 makes it more difficult to force the plug 11 into the blood vessel 100, and therefore, also minimizes the probability of arterial penetration.

Figure 4A:
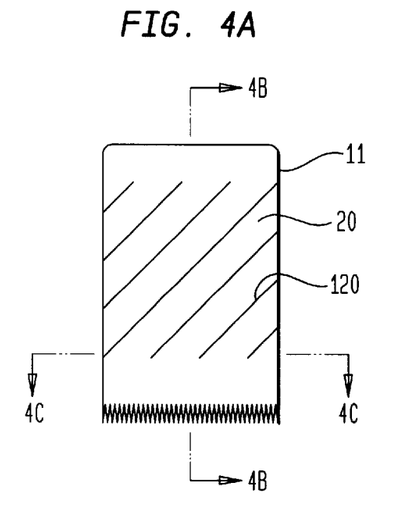
FIG. 4A illustrates a plan view of an alternate embodiment of the plug comprising helical lacerations.
Figure 4B:
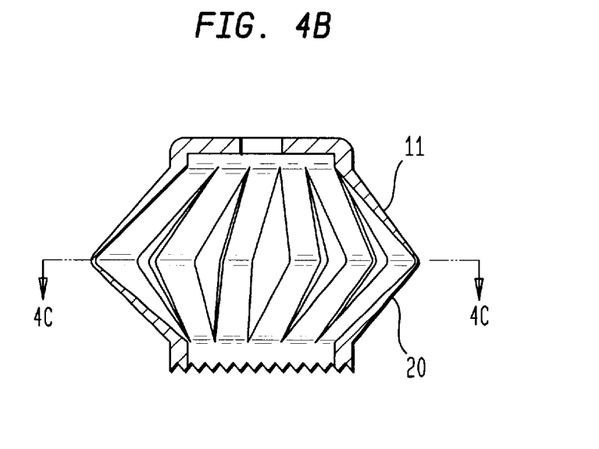
FIG. 4B illustrates a longitudinal cross sectional view of the plug with helical lacerations in its semi-collapsed form taken along lines 4B—4B in FIG. 4A.
Figure 4C:
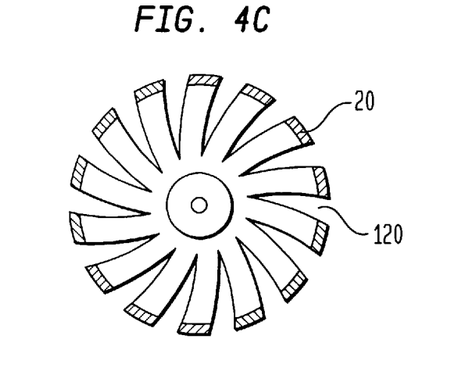
FIG. 4C is a transverse cross section of the plug in FIG. 4A in a collapsed state taken along lines 4C—4C.
Figure 5:
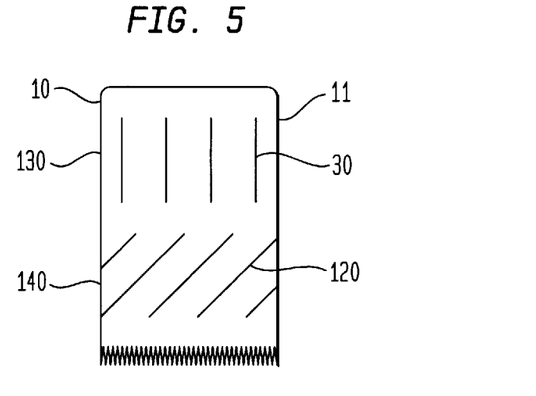
FIG. 5 is a plan view of the plug having two collapsible portions.

FIG. 4A illustrates an alternate embodiment of the improved hemostatic plug 11 identical to the plug illustrated in FIG. 1A except comprising helical lacerations 120 rather than longitudinal lacerations 30. FIG. 4B illustrates a longitudinal cross section of the plug 11 with helical lacerations 120 in its semi-collapsed form taken along line 4B—4B in FIG. 4A. The distance between the proximal and distal ends has decreased and the wings 20 have radially expanded. Furthermore, the distal fretted end has mushroomed. FIG. 4C is a transverse cross section of the plug 11 in FIG. 4B in its collapsed state taken along lines 4C—4C. As can be seen in FIG. 4C, in its collapsed form the average distance between the wings 20 in the plug 11 having helical lacerations 120 is less than the averaged distance between the wings 20 in the plug 11 having longitudinal lacerations 30 (as seen in FIG. 1E). Depending on the insertion site of the plug 11, a plug having helical lacerations with its tightly spaced wings, may be a more appropriate anchor than a plug having longitudinal lacerations. Note that the number, length, and distance between the longitudinal lacerations, and the pitch, number, and length of the helical lacerations will affect both the anchorability of the plug 11 and also the collapsibility of the plug 11. Note further that the plug 11 may be designed to have more than one collapsible portion. This may be accomplished by having sets of shorter lacerations with non-laceration portions between them, as illustrated in FIG. 5. FIG. 5 illustrates the plug 11 having two collapsible portions, a proximal collapsible portion 130 and a distal collapsible portion 140. The proximal collapsible portion 130 comprises longitudinal lacerations 30 and the distal collapsible portion 140 comprises helical lacerations 120. Note that both the longitudinal lacerations 30, as illustrated in FIGS. 1A and 5, and the helical lacerations 120, as illustrated in FIGS. 4A and 5, do not have to be equally spaced around the plug 11. Rather the number, length, width, pitch, and spacing of the lacerations may be controlled to created the desired buckling effect.

Figure 6:
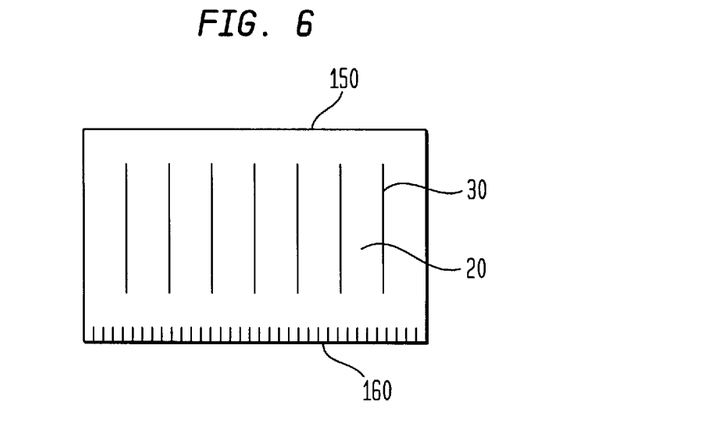
FIG. 6 is a plan view of collagen sheet of paper, used to fabricate the plug, with lacerations in it and a fretted end.

The plug 11 is fabricated by rolling a collagen paper 150, as illustrated in FIG. 6, having short slits 160 on its distal end and appropriately sized longitudinal lacerations 30 (or alternatively helical lacerations 120), around a mandrel (not shown) to form a tube of desired thickness. The collagen paper 150 is made from a thin sheet of collagen. The tighter the collagen paper 150 is rolled the stiffer the plug 11 becomes and the more axial pressure needs to be applied to initiate collapse of the plug 11.

Figure 7:
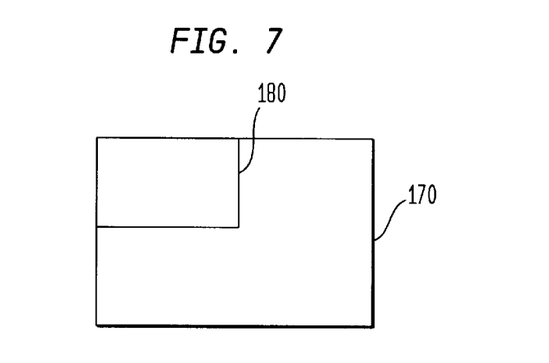
FIG. 7 is a plan view of a smaller sheet of collagen paper laid over a larger sheet of collagen paper.
Figure 8:
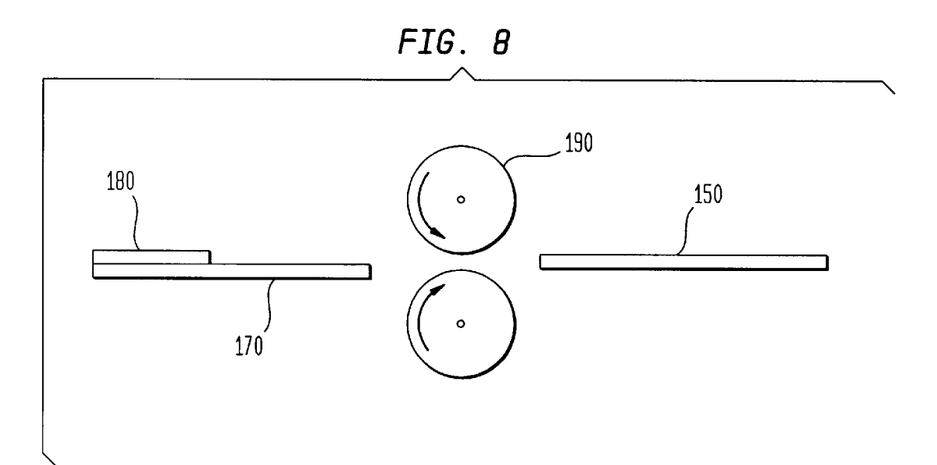
FIG. 8 illustrates the collagen sheet illustrated in FIG. 7 being rolled into a single collagen paper of uniform thickness and varying density.

The collagen paper 150 is fabricated to have varying densities by adjusting the amount and position of the raw collagen prior to compressing the material down to a sheet. An example of this is to take a first rectangular sheet 170 of uncompressed collagen, as illustrated in FIG. 7, and lay a second sheet 180 one quarter the size of the first rectangular sheet 170 over it, aligning two edges. Next, compress this substrate to a uniform thickness by passing them through rollers 190, as illustrated in FIG. 8, to form a sheet of varying density uniform thickness collagen paper 150. Where the two sheets overlapped the density will be double and the stiffness and blood absorption time will be greater. As discussed above, lacerations are then made in the collagen paper 150, shown in FIG. 6, and to enhance the mushrooming effect, the distal end of the plug is fretted. This sheet is then used to form a plug by wrapping it around a mandrel with the denser end located proximally. The less dense distal end will be softer and more absorbent than the proximal denser end allowing it to become more compliant and mushroom when contacting the exterior wall of the blood vessel 100 at the puncture 101 (FIG. 2). When the fretted end contacts the exterior surface of the artery, as illustrated in FIG. 2, it fans out covering a large surface area. Minimal axial compressive force is required to achieve this mushrooming effect. The length, width, and pitch of the slits 160 (shown in FIG. 6) at the distal end may be varied according to the desired effect.

Figure 9:
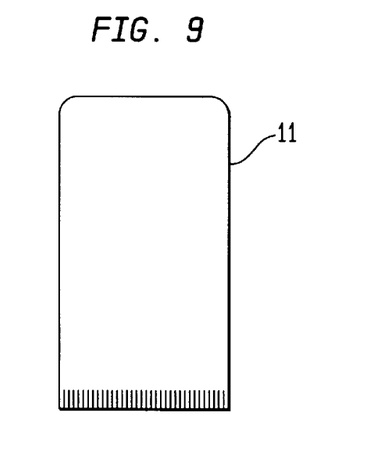
FIG. 9 is a plan view of the plug without lacerations.
Figure 10:
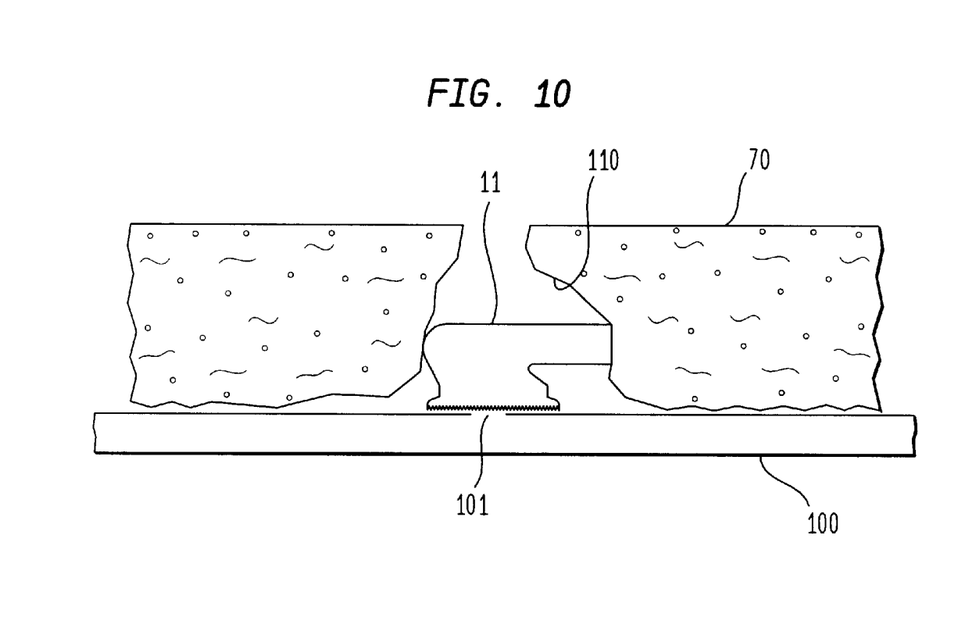
FIG. 10 is a cross sectional view of a patient's leg and the plug, as illustrated in FIG. 9, in its collapsed form inserted within the patient's leg.

Alternate embodiments of the plug 11 rely on the rolling of the collagen paper rather than the location, spacing, and pitch of lacerations in the collagen paper, to create the collapsibility property. FIG. 9 illustrates the plug 11, similar to its illustration in FIGS. 1A and 4A, except lacking lacerations. FIG. 10 illustrates said plug 11, already inserted into a patient's leg 70, in its collapsed form. The proximal end of the body of the plug 11 operates as an anchor by lodging between the blood vessel 100 and the surrounding tissue 110. The plug 11, if not lodged between the blood vessel 100 and the surrounding tissue 110, would spring back (by means of a restoring force) to its original shape. This restoring force maintains pressure on the puncture 101 in the blood vessel 100. The following steps are required to properly position and secure the plug 11. The plug 11 is inserted into the patient's leg 70 such that the distal end of the plug 11 contacts the puncture 101 in the blood vessel 100. Next a threshold force is applied to the plug causing it to buckle. The plug is then bent into a V-shape by forcing the proximal end of the plug towards the distal end. While maintaining this V-shape the proximal end of the plug 11 is lodged between the blood vessel 100 and surrounding tissue 110 so as to fix the proximal end.

Figure 11:
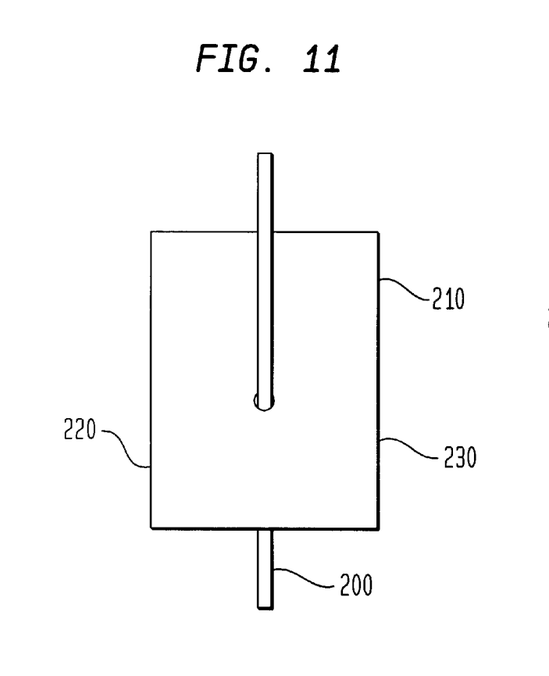
FIG. 11 is a plan view of a sheet of collagen paper with a removable tube inserted through its center.
Figure 12:
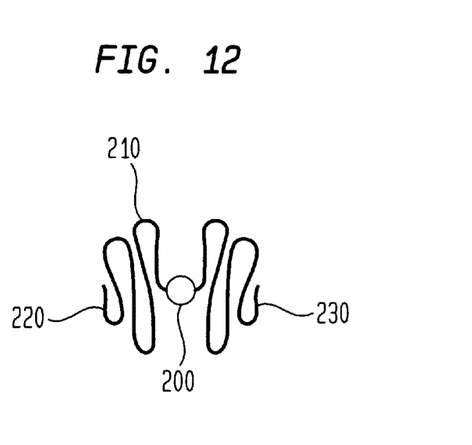
FIG. 12 is a top view of the sheet of paper illustrated in FIG. 11 with portions of the sheet to the left and right of the removable tube folded.
Figure 13:
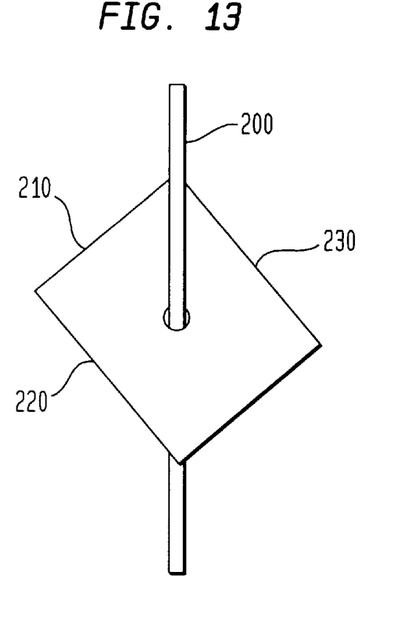
FIG. 13 is a plan view of the sheet of collagen paper illustrated in FIG. 11 rotated ninety degrees.
Figure 14:
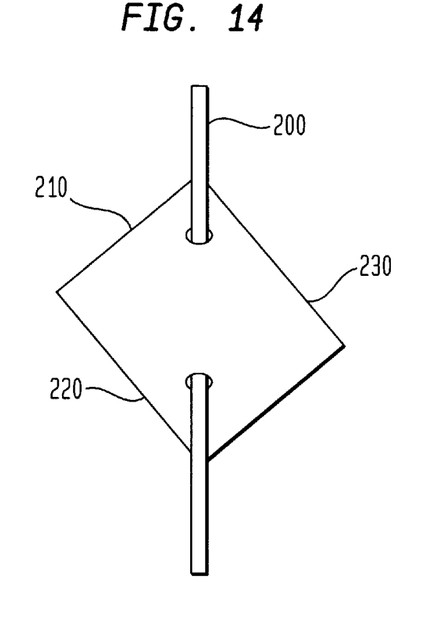
FIG. 14 is a plan view of the sheet of collagen paper illustrated in FIG. 13 with the removable tube piercing the collagen sheet in two locations rather than just one location.

The plug 11, illustrated in FIG. 9, is formed by rolling collagen paper about a removable tube 200, as illustrated in FIG. 11. The removable tube 200 is inserted through the middle of a collagen sheet 210 having a left side 220 and a right side 230. The collagen sheet 210 is folded such that the left side 220 and the right side 230 are in contact. Next the collagen paper is rolled about the removable tube 200. Alternatively, the paper on both sides of the collagen sheet 210 can be folded resulting in a plug having a top view as illustrated in FIG. 12. A collapsible plug 11 having different properties can be formed by rotating the collagen paper ninety degrees (or a different angle) before rolling or folding, as illustrated in FIG. 13, or by having the removable tube 200 pierce the collagen paper 150 in two or more locations before rolling or folding, as illustrated in FIG. 14. Each of the above described plug fabrication schemes will produce plugs with varying collapsibility and blood saturation rate properties. The removable tube 200 is use as a mandrel to maintain the shape of the plug 11 during fabrication. A preliminary step to insertion of the plug 11 involves inserting the guide wire 80 through the removable tube 200 and then removing the removable tube 200 by pulling it away from the patient toward the proximal end of the guide wire 80.

Figure 15:
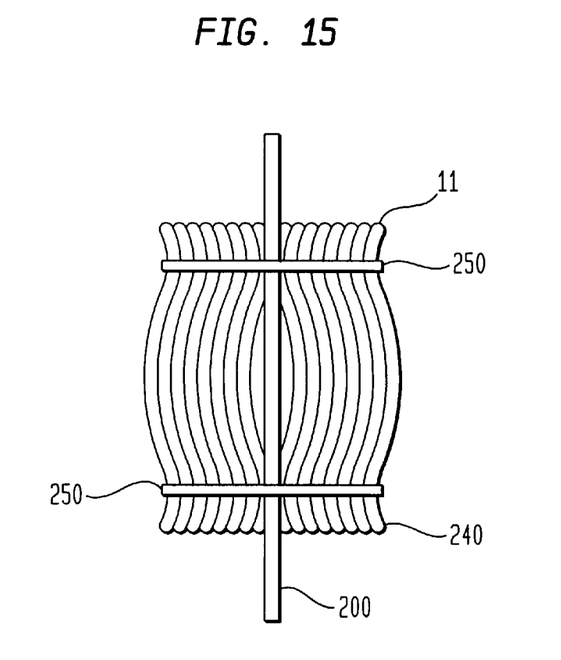
FIG. 15 is a plan view of an alternate embodiment of the plug comprising thin strips bundled about the removable tube.
Figure 16:
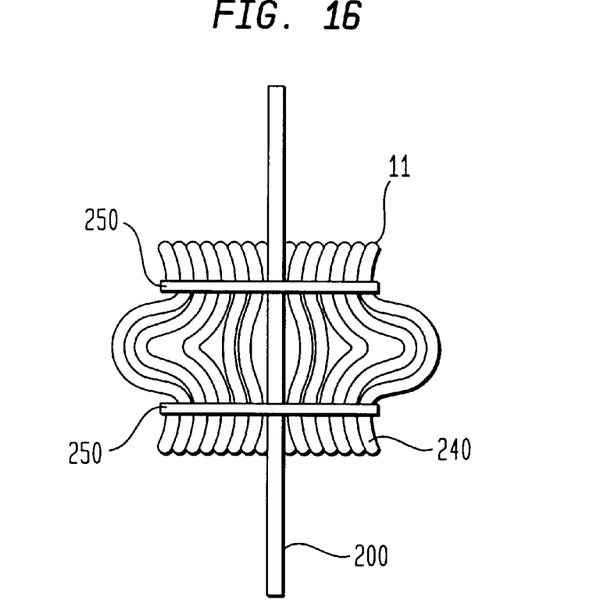
FIG. 16 is a plan view of the plug, as illustrated in FIG. 15, in a semi-collapsed form.

FIG. 15 illustrates yet another alternate embodiment of the plug 11. The plug 11 comprises thin parallel strips 240 of collagen which are bundled about the removable tube 200 by wrapping a distal portion and a proximal portion of the thin strips 240 with a band 250. The plug 11 resembles a broom except that only one end of the bristles are attached to the handle of a broom. After a threshold axial insertion force is applied to the plug 11 the thin strips 240 collapse and anchor between the blood vessel 100 and surrounding tissue 110, similar to the collapsed plug 11 with lacerations illustrated in FIG. 3. FIG. 16 illustrates the plug 11 in a semi-collapsed state. Note that the filaments have buckled and radially expanded and that the distance between the distal and proximal ends has decreased. The collapsibility of the plug 11 may be controlled by varying the width, thickness, or diameter (if circular strips are used) of the strips 240. Furthermore, the width, thickness, or diameter of the thin strips 240 may vary along the length of the strips 240. Also note that the lengths of the strips 240 may be controlled so as to create a distal end that is contoured to the shape of the punctured artery, thereby optimizing arterial surface area coverage. Similarly, the diameter or thickness and width of the distal end of the strips 240 may be made smaller, making the plug 11 more pliable, so as to allow the distal end of the plug 11 to conform to the shape of a blood vessel upon contact. Similar to the insertion procedure described above for the other alternate embodiments of the plug 11 described the removable tube 200 is removed prior to insertion of the plug 11.

Figure 17:
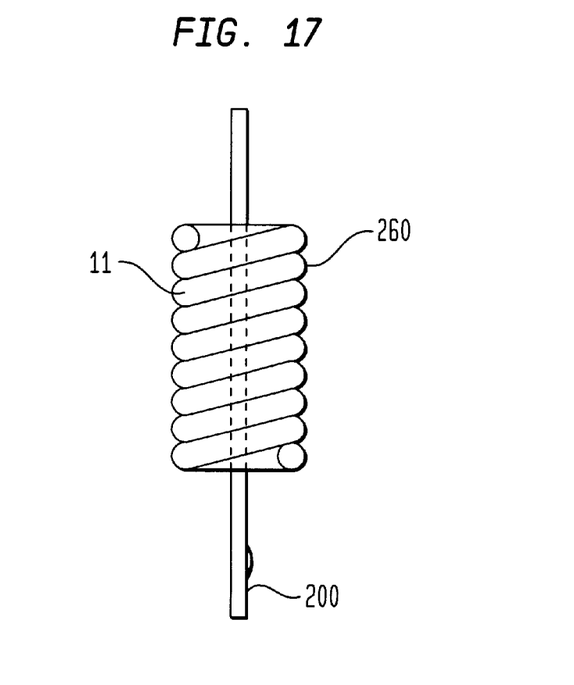
FIG. 17 is a plan view of an alternate embodiment of the plug comprising a helical filament coiled about the removable tube.
Figure 18:
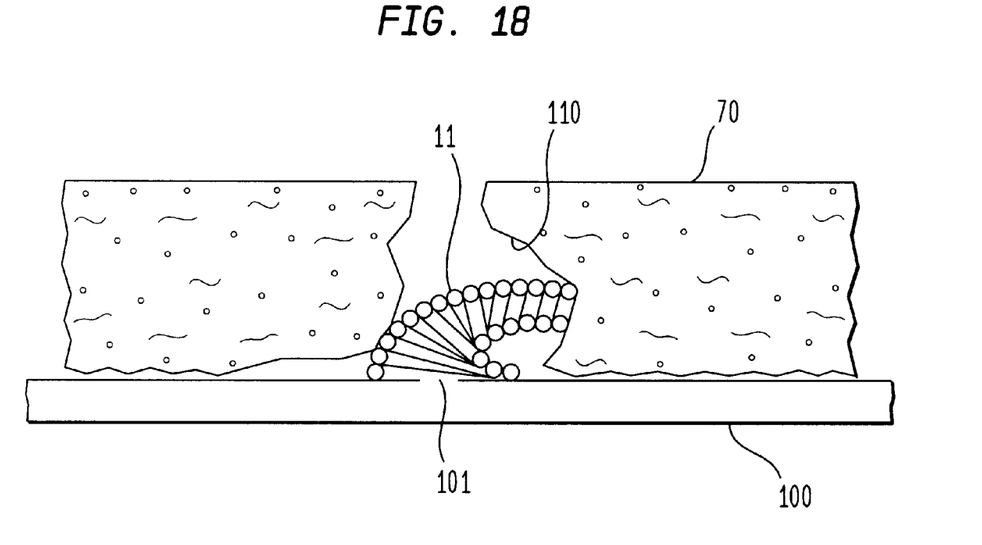
FIG. 18 is a cross sectional view of the patient's leg with the plug as illustrated in FIG. 17 inserted within said patient's leg.

FIG. 17 illustrates another alternate embodiment of the plug 11. The plug 11 comprises a collagen filament 260 wrapped around the removable tube 200 in a rope like manner. Once inserted into the tissue tract, the plug 11 may be unraveled at the distal end by twisting the proximal end and thus cover a larger surface area at the puncture 101. FIG. 18 illustrates a cross sectional view of the plug 11 inserted into the patient's leg 70. Insertion of the plug 11 comprises the following steps. First, the guide wire 80 is inserted through the removable tube 200 and the removable tube 200 is removed. Next the plug 11 is advanced forward into the patient's leg 70 such that the distal end contacts the puncture 101 in the blood vessel 100 and force is applied until the plug 11 buckles. At this point the force is relieved so as to allow the plug 11 spring back into its original shape. The plug 11 is then unraveled at the distal end by twisting the proximal end. The distal end is lodged in surrounding tissue 110 directly above the arterial puncture 101 and therefore remains fixed. The purpose of unraveling the plug 11 is to increase the diameter of the distal end of the plug 11, and therefore, allow for greater surface area sealing coverage of the puncture 101. The unraveling torque applied to the distal end of the plug 11 is maintained as axial force is applied once again to buckle the plug 11. After buckling the proximal end becomes lodged into the surrounding tissue 110 thereby keeping the proximal end of the plug 11 fixed and thus maintaining continuous pressure on the puncture 101.

Figure 19:
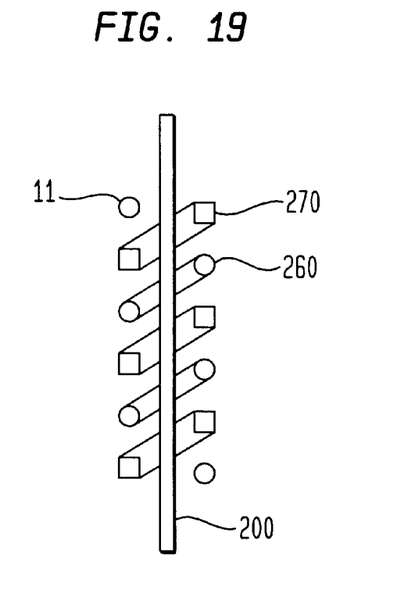
FIG. 19 is a longitudinal cross sectional view of an alternate embodiment of the plug comprising the collagen filament and a collagen sponge filament coiled together about the removable tube.

Alternatively, the rope-like plug 11 may be made up of collagen filaments 260 and compressed collagen sponge filaments 270 coiled together, as illustrated in FIG. 19. FIG. 19 illustrates a longitudinal cross section of such a plug 11. The collagen filaments 260 are useful for puncture 101 closure because of their hemostatic properties. The collagen sponge filaments 270 expand upon exposure to blood and are therefore useful to provide continuous pressure on the puncture 101.

What is claimed is:

1. A hemostatic plug for sealing a puncture in a blood vessel said plug having a longitudinal axis, a proximal end, and a distal end, said plug comprising a tube having an inner and outer surface and at least one collapsible portion between said proximal and distal ends capable of collapsing upon application of opposing threshold longitudinal forces said collapsible portion having proximal and distal ends and one or more lacerations which extend in length from the proximal to the distal end of the collapsible portion and extend in thickness from the inner surface to the outer surface of the plug and a plurality of wings which are strips of the plug located between the lacerations and which extend from the distal to the proximal end of the collapsible portion, the wings buckle upon application of a threshold force.

2. The plug as claimed in claim 1 wherein the distal end of the plug is fretted.

3. The plug as claimed in claim 1 wherein the plug is made from collagen.

4. The plug as claimed in claim 1 wherein the lacerations are parallel to the longitudinal axis of the plug.

5. The plug as claimed in claim 1 wherein the lacerations are helical with respect to the longitudinal axis of the plug.

6. A plug for sealing a hole in a bodily vessel, said plug having a longitudinal axis, a proximal end, and a distal end, said plug comprising at least one collapsible portion capable of collapsing upon application of opposing longitudinal threshold forces, said collapsible portion comprising two or more wings, said wings being strips of the plug that buckle upon application of the threshold force and lodge into surrounding tissue for maintaining temporary continued pressure on the hole in the bodily vessel.

7. The plug as claimed in claim 6 wherein the bodily vessel is a blood vessel.

8. The plug as claimed in claim 6 wherein the plug is a hemostatic plug.

9. The plug as claimed in claim 6 comprising a tube having an inner surface, an outer surface, and a longitudinal axis.

10. The plug as claimed in claim 9 wherein the collapsible portion comprises one or more lacerations and wherein the plug has a longitudinal axis.

11. The plug as claimed in claim 10 wherein the plug comprises a tube having an inner and outer surface and wherein the lacerations have a predetermined length and extend from the outer surface of the tube to a point between the inner and outer surface.

12. The plug as claimed in claim 10 wherein the plug comprises a tube having and inner and outer surface and wherein the lacerations have a predetermined length and extend from the inner surface of the tube to a point between the inner surface and outer surface.

13. The plug as claimed in claim 10 wherein the plug comprises a tube having an inner and outer surface and wherein the lacerations are parallel to the longitudinal axis of the tube.

14. The plug as claimed in claim 10 wherein the lacerations are helical relative to the longitudinal axis of the tube.

* * * * *